United States Patent [19]

Mar

[11] Patent Number: 4,726,369
[45] Date of Patent: Feb. 23, 1988

[54] TOOL AND METHOD FOR STEERING AN ANGIOPLASTY GUIDE WIRE

[75] Inventor: Craig E. Mar, Fremont, Calif.

[73] Assignee: Advanced Cardiovascular Systems, Inc., Mountain View, Calif.

[21] Appl. No.: 891,151

[22] Filed: Jul. 31, 1986

[51] Int. Cl.⁴ ............................................. A61B 7/00
[52] U.S. Cl. ............................. 128/303 R; 128/330; 128/340; 128/657
[58] Field of Search ............................ 128/656-658, 128/772, 303 R, 330, 340; 604/170, 165, 159; 226/127; 24/131 C, 265 C; 81/44

[56] References Cited

U.S. PATENT DOCUMENTS

| | | | |
|---|---|---|---|
| 3,045,676 | 7/1962 | Slaten | 128/303 R |
| 3,537,451 | 11/1970 | Beck et al. | 604/165 |
| 4,598,708 | 7/1986 | Beranek | 128/303 R |
| 4,615,472 | 10/1986 | Nash | 604/159 |

Primary Examiner—Dalton L. Truluck
Assistant Examiner—Denise Whelton
Attorney, Agent, or Firm—Fulwider, Patton, Rieber, Lee & Utecht

[57] ABSTRACT

Tool and method for turning or steering an angioplasty guide wire as it is inserted into the body of a patient. The tool has a body of resilient material with a slit in which the guide wire is received. The slit opens through the side of the body, and the tool can be attached to the wire from the side. An outer sleeve encircles the resilient body, with a slot through which the wire is inserted and removed, and the resilient body is compressed by the sleeve to hold the slit closed and grip the wire tightly. The wire is turned or steered by gripping the outer sleeve and rotating the tool about its axis.

8 Claims, 3 Drawing Figures

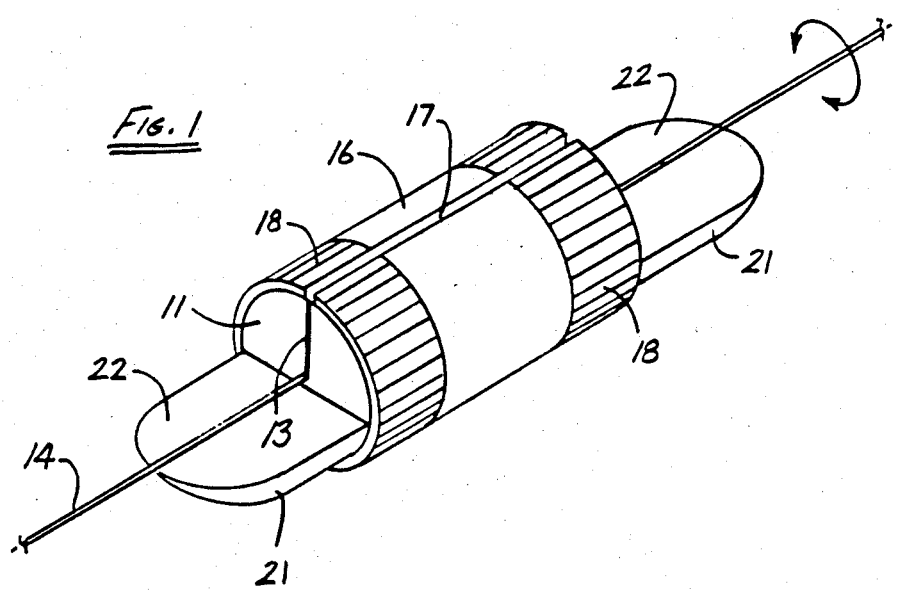
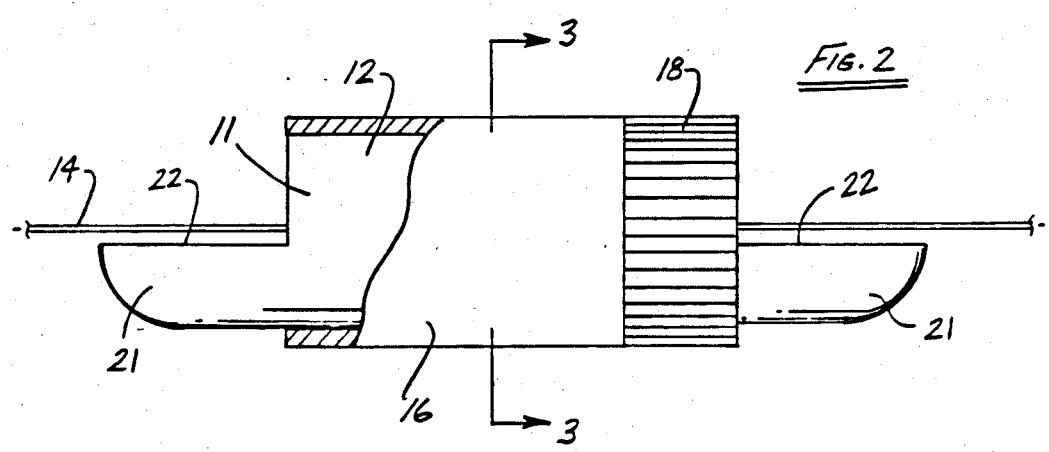
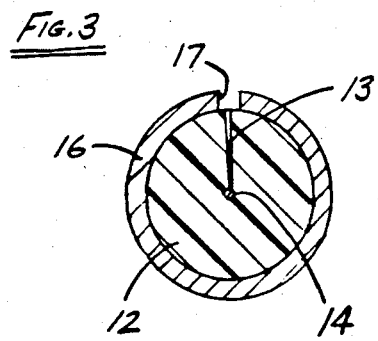

TOOL AND METHOD FOR STEERING AN ANGIOPLASTY GUIDE WIRE

This invention pertains generally to medical appliances, and more particularly to a tool and method for inserting an angioplasty guide wire into a patient.

Angioplasty guide wires are frequently provided with shaped tips and turned about their axes as they are inserted to position them in a desired vessel in a patient's body. The guide wires are relatively fine and difficult to grip between the fingers.

Heretofore, pin vises have sometimes been used for gripping guide wires. This is somewhat inconvenient, however, because the pin vise must be installed from the end of the wire and slid along the wire to the desired position.

It is in general an object of the invention to provide a new and improved tool for steering an angioplasty guide wire as it is inserted into a patient.

Another object of the invention is to provide a tool and method of the above character wherein the tool is attached to the guide wire from the side.

These and other objects are achieved in accordance with the invention by providing a tool having an elongated body of resilient material with a longitudinally extending slit opening through one side thereof for receiving and gripping the guide wire. A sleeve encircles the resilient body and is affixed thereto to provide means by which the tool can be gripped and rotated about the axis of the wire. The sleeve has a lontudinally extending slot through which the guide wire can pass to the slit in the resilient body as the tool is applied to the guide wire from the side. The sleeve compresses the resilient body to close the slit tightly about the wire, and longitudinally extending ears facilitate seating of the wire in the slit.

FIG. 1 is an isometric view of one embodiment of a guide wire steering tool according to the invention in connection with a guide wire.

FIG. 2 is a side elevational view, partly broken away, of the embodiment of FIG. 1.

FIG. 3 is a cross-sectional view taken along line 3—3 in FIG. 2.

As illustrated in the drawings, the tool comprises a generally cylindrical body 11 of resilient material having a central section 12 in which a radial slit 13 is formed for receiving and gripping a guide wire 14. The slit extends longitudinally of the central body section and opens through one side of the body. The body is formed of a material such as santoprene rubber which is resilient and has a relatively high coefficient of friction for gripping the wire.

A cylindrical sleeve 16 encircles the central section of body 11 and has a longitudinally extending slot 17 which is aligned with slit 13 to permit insertion and removal of the guide wire. The sleeve is fabricated of a relatively rigid material such as polycarbonate or ABS plastic, and it compresses the resilient body to hold the slit closed tightly about the guide wire. The sleeve is thus affixed to the resilient body, and the guide wire can be turned by gripping the sleeve and rotating it about its axis. The end portions 18 of the sleeve are ribbed or fluted to provide a better grip.

Longitudinally extending ears 21 project from the ends of central body section 12 and provide means by which the guide wire can be more readily be drawn into slit 13. The ears are formed as an integral part of body 11, and they are positioned on the side of the body opposite the slit. The ears have a generally semi-cylindrical shape, with generally planar upper surfaces 22 generally perpendicular to slit 13. These surfaces are spaced a short distance below the axis of the body and the bottom of the slit.

Operation and use of the tool, and therein the method of the invention, are as follows. The tool is attached to the guide wire from the side by placing the wire in slot 17 and pressing it into slit 13. The wire is readily seated in the slit by squeezing it and ears 21 together, for example, between the thumbs and fingers of the hands. If necessary, the ears can be bent back away from the slit to further seat the wire in the slit.

Once the tool has been attached to the wire, sleeve 16 can be gripped by the doctor and rotated to turn and steer the guide wire as it is inserted into a patient. During the insertion process, the tool can be removed and repositioned on the wire as desired. The tool is removed simply by pulling the wire out of slit 13 through slot 17. If necessary, the doctor can squeeze the sleeve slightly to further compress the resilient body and increase the grip upon the wire.

The invention has a number of important features and advantages. It can be attached to a guide wire from the side and any point along the wire. It is easy to install and remove, and it gives the doctor good control over the rotational position of the wire.

It is apparent that a new and improved tool and method for steering an angioplasty guide wire have been provided. While only certain presently preferred embodiments have been described in detail, as will be apparent to those familiar with the art, certain changes and modifications can be made without departing from the scope of the invention as defined by the following claims.

What is claimed is:

1. In a tool for turning an angioplasty guide wire to steer the wire as it is inserted into a patient: a body of resilient material having a longitudinally extending slit opening laterally through one side thereof for receiving and gripping the wire, and a relatively rigid sleeve encircling body and compressing the resilient material to hold the slit closed tightly about the wire, said sleeve having a longitudinally extending slit through which the wire can pass and an outer surface adapted to be gripped by a person using the tool to rotate the guide wire.

2. The tool of claim 1 wherein the resilient body includes a generally cylindrical central portion in which the slit is formed and a pair of generally semicylindrical end portions projecting longitudinally from the ends of the central portion, said end portions having generally planar surfaces generally perpendicular to the slit against which the guide wire can be pressed as it is inserted into the slit.

3. In a tool for turning an angioplasty guide wire to steer the wire as it is inserted into a patient: an axially elongated generally cylindrical body of resilient material having a radial slit through one side thereof for receiving and gripping the guide wire, and a relatively rigid outer sleeve which compresses the resilient body and holds the slit closed tightly, said sleeve being adapted to be gripped by a person using the tool to rotate the guide wire, said sleeve having a longitudinally extending slot aligned with the slit in the resilient body through which the guide wire can pass as the tool is attached to the guide wire from the side.

4. The tool of claim 3 including a pair of longitudinally extending ears projecting from the ends of the resilient body against which the guide wire can be drawn as the tool is attached to the wire.

5. The tool of claim 4 wherein the longitudinally extending ears comprise semi-cylindrical members formed integrally with the resilient body and being positioned toward the opposite side of the body from the radial slit with generally planar surfaces generally perpendicular to the slit.

6. In a method of steering an angioplasty guide wire with a tool having a body of resilient material with a longitudinally extending slit opening through one side thereof and a relatively rigid sleeve encircling the resilient body and compressing the resilient material to hold the slid closed, the steps of: attaching the tool to the guide wire by pressing the wire into the closed slit so that the wire is gripped and held securely by the resilient material, and turning the sleeve to turn the guide wire.

7. The tool of claim 1 wherein the end portions of the relatively rigid sleeve are ribbed to facilitate gripping of the sleeve.

8. The tool of claim 3 wherein the end portions of the relatively rigid sleeve are ribbed to facilitate gripping of the sleeve.

* * * * *

UNITED STATES PATENT AND TRADEMARK OFFICE
CERTIFICATE OF CORRECTION

PATENT NO. : 4,726,369

DATED : February 23, 1988

INVENTOR(S) : Craig E. Mar

It is certified that error appears in the above-identified patent and that said Letters Patent are hereby corrected as shown below:

Column 2, line 45, change "slit" to --slot--.

Column 4, line 2, change "slid" to --slit--.

Signed and Sealed this

Ninth Day of August, 1988

Attest:

DONALD J. QUIGG

*Attesting Officer*    *Commissioner of Patents and Trademarks*